(54) PROCESS FOR HOT STRETCHING BRAIDED LIGATURES

(76) Inventors: Robert L. Washington, 517 Kinney Mill Rd., Mt. Airy, GA (US) 30563; Richard T. Entrekin, 6618 Pinehurst Dr., San Angelo, TX (US) 76904

(*) Notice: Subject to any disclaimer, the term of this patent is extended or adjusted under 35 U.S.C. 154(b) by 0 days.

This patent is subject to a terminal disclaimer.

(21) Appl. No.: 09/188,588

(22) Filed: Nov. 9, 1998

(51) Int. Cl.⁷ ............... A61B 17/04; D01D 5/30
(52) U.S. Cl. ............. 606/228; 606/230; 606/231; 264/172.11; 264/176.1; 264/177.19
(58) Field of Search .................. 606/228, 229, 606/230, 231; 264/172.11, 177.19, 176.1

(56) References Cited

U.S. PATENT DOCUMENTS

| | | | |
|---|---|---|---|
| 3,130,728 | 4/1964 | Pearson et al. | 128/335.5 |
| 3,257,702 | 6/1966 | Kurtz . | |
| 3,297,033 | 1/1967 | Schmitt et al. | 128/335.5 |
| 3,379,091 | 4/1968 | Kurtz . | |
| 3,379,552 | 4/1968 | Kurtz . | |
| 3,468,853 | 9/1969 | Schmitt . | |
| 3,531,561 | 9/1970 | Trehu | 264/210 |
| 3,565,077 | 2/1971 | Glick | 128/335.5 |
| 3,626,948 | 12/1971 | Glick et al. | 128/335.5 |
| 3,636,956 | 1/1972 | Schneider | 128/335.5 |
| 3,754,069 | 8/1973 | Adams et al. . | |
| 3,772,420 | 11/1973 | Glick et al. | 264/102 |
| 3,838,524 | 10/1974 | Hencke et al. . | |
| 3,839,524 | 10/1974 | Adams et al. | 261/131 |
| 3,849,185 | 11/1974 | Shepherd et al. | 117/161 |
| 3,942,532 | 3/1976 | Hunter et al. | 128/335.5 |
| 3,949,755 | 4/1976 | Vauquois | 128/335.5 |
| 4,014,973 | * 3/1977 | Thompson | 606/228 |
| 4,024,871 | 5/1977 | Stephenson | 128/335.5 |
| 4,027,676 | 6/1977 | Mattei | 128/335.5 |
| 4,043,344 | 8/1977 | Landi et al. | 128/335.5 |
| 4,047,533 | 9/1977 | Perciaccante et al. | 128/335.5 |
| 4,052,988 | 10/1977 | Doddi et al. | 128/92 |
| 4,510,934 | 4/1985 | Batra | 128/335.5 |
| 4,662,886 | 5/1987 | Moorse et al. | 623/13 |
| 4,942,875 | 7/1990 | Hlavacek et al. | 606/230 |
| 4,946,467 | 8/1990 | Ohi et al. | 606/228 |
| 4,959,069 | 9/1990 | Brennan et al. | 606/228 |
| 4,983,180 | 1/1991 | Kawai et al. | 606/230 |
| 5,007,922 | * 4/1991 | Chen et al. | 606/228 |
| 5,010,145 | 4/1991 | Ikada et al. . | |
| 5,019,093 | * 5/1991 | Kaplan et al. | 606/228 |
| 5,037,429 | 8/1991 | Hermes et a. | 606/230 |
| 5,051,272 | 9/1991 | Hermes et al. | 427/2 |

(List continued on next page.)

FOREIGN PATENT DOCUMENTS

| | | | |
|---|---|---|---|
| 835026 | 2/1970 | (CA) . | |
| 2 115 108 | 10/1994 | (CA) . | |
| 29 49 920 A1 | 3/1981 | (DE) | A61L/17/00 |
| 113 739 | 7/1983 | (EP) . | |
| 0 241 252 | 10/1987 | (EP) | A61L/27/00 |
| 0 513 335 | 4/1991 | (EP) . | |
| A 0472260 | 2/1992 | (EP) | A61L/17/00 |
| 0 523 743 | 7/1992 | (EP) . | |
| 752443 | 7/1956 | (GB) . | |
| 1091669 | 11/1967 | (GB) | A61L/17/00 |
| 1332505 | 10/1973 | (GB) | D01F/7/04 |
| 2 008 135 A | 5/1979 | (GB) | C08G/63/76 |
| 2 082 213 A | 3/1982 | (GB) | D04C/1/12 |
| 2 159 846 A | 12/1985 | (GB) | D02G/3/36 |
| 107441 | 8/1979 | (JP) . | |
| 112151 | 8/1979 | (JP) . | |
| 500127 | 11/1980 | (JP) . | |
| WO 92/10137 | 6/1992 | (WO) | A61B/17/00 |

Primary Examiner—Gary Jackson

(57) ABSTRACT

The present invention provides an apparatus and process for improving the properties of braided ligature by hot stretching the braid.

23 Claims, 2 Drawing Sheets

U.S. PATENT DOCUMENTS

| | | | |
|---|---|---|---|
| 5,059,213 | 10/1991 | Chesterfield et al. | 606/228 |
| 5,123,912 | 6/1992 | Kaplan et al. | 606/230 |
| 5,133,738 | 7/1992 | Korthoff et al. | 606/224 |
| 5,181,923 * | 1/1993 | Chesterfield et al. | 606/228 |
| 5,261,886 | 11/1993 | Chesterfield et al. | 606/228 |
| 5,306,289 | 4/1994 | Kaplan et al. | 606/228 |
| 5,451,461 * | 9/1995 | Broyer | 606/228 |
| 5,456,696 * | 10/1995 | Lui | 606/228 |
| 5,456,697 | 10/1995 | Chesterfield et al. | 606/228 |
| 5,483,009 * | 1/1996 | Jiang | 525/417 |
| 5,549,907 * | 8/1996 | Lui et al. | 424/443 |
| 5,618,313 * | 4/1997 | Roby et al. | 606/230 |
| 5,797,962 * | 8/1998 | Tomihata et al. | 606/228 |
| 5,843,574 * | 12/1998 | Suryadevara et al. | 428/364 |
| 5,871,502 * | 2/1999 | Suryadevara et al. | 606/228 |

* cited by examiner

US 6,264,674 B1

PROCESS FOR HOT STRETCHING BRAIDED LIGATURES

FIELD OF THE INVENTION

The present invention relates to an apparatus and process improving the properties of braided fibers, more particularly an apparatus and process for hot stretching braided surgical ligatures.

BACKGROUND OF THE INVENTION

Multifilament sutures are generally made by braiding yarns into a braided structure. Appropriate braided constructions for surgical sutures have been described in U.S. Pat. Nos. 5,019,093; 4,959,069 and 5,059,213 (all incorporated by reference herein). After the braided construction has been made the braid is cleaned by scouring and generally compacted by hot stretching the braid multifilament.

One suitable means for hot stretching braided constructions is illustrated in FIG. 1. A spool of braided multifilament is attached to a tensioning device. The braided multifilament is then wound around feed rolls (4 and 6 respectively) and threaded through heated plates 8. The braided multifilament is then drawn by draw rolls 10 and 12 and collected on take up spool 14. The drawing is accomplished by rotating the draw rolls faster than the feed rolls to stretch the braided multifilament. Generally the braided multifilament are drawn in the range of from about 10 to about 20 percent. The amount that the suture is to be drawn depends on the size of the suture, the material the suture is made of and the braid construction. Similarly the temperature and residence time for the braided multifilament would have between the heated plates would also depend on these same factors.

Unfortunately, this process and apparatus although effective in providing a hot stretched braided suture resulted in two potential defects being introduced into the braided multifilament sutures. The first defect is slight increase in the number of sutures that do not pass quality assurance strength tests. The second defect is a tendency for the braid to have irregular bunching in the braid.

Therefore, it is an object of the present invention to provide a method and apparatus for hot stretching braided multifilament sutures that results in little or no strength loss associated with hot stretching. Alternatively, it is an object of the present invention to provide an apparatus and process for hot stretching braided multifilament sutures which reduces or eliminates bunching in braided multifilament sutures.

SUMMARY OF THE INVENTION

The present invention provides an improved process for hot stretching braided multifilaments. This process comprising advancing a braided multifilament to a first heating zone, then drawing the braided multifilament while heating the braided multifilament thereafter heat setting the braided multifilament to provided a braided suture.

DETAILED DESCRIPTION

Figure 2:
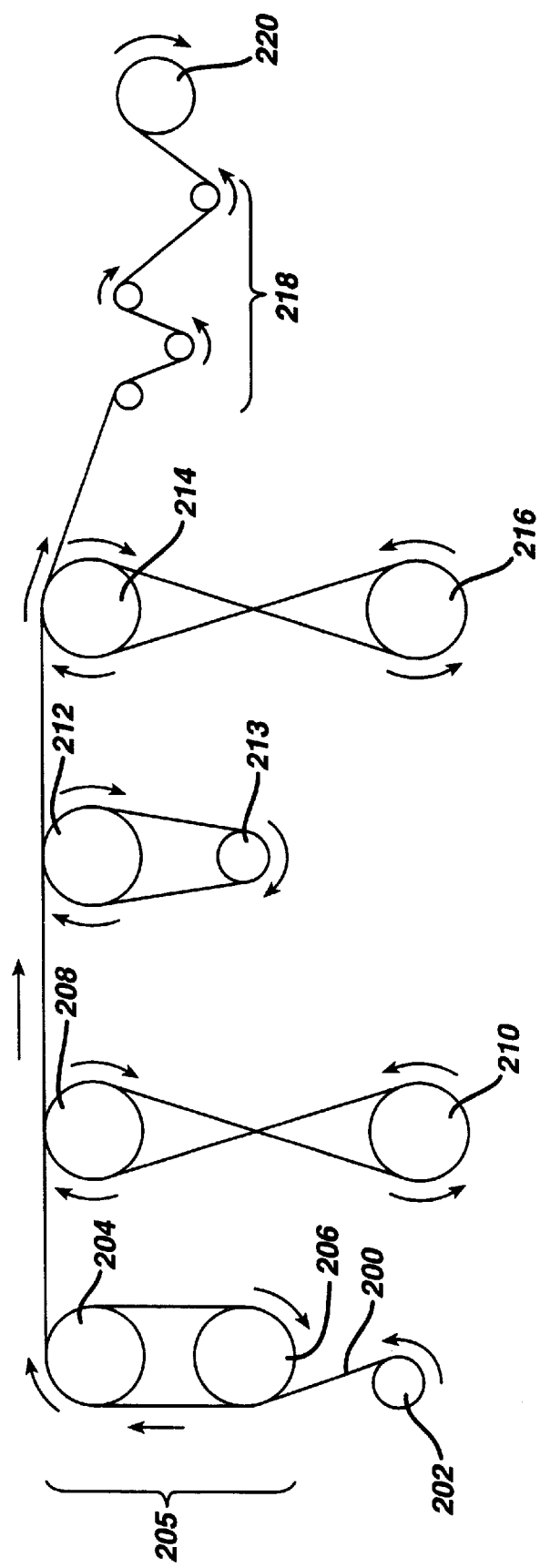
FIG. 2 illustrates the improved hot stretching apparatus, which both draws and relaxes the multifilament sutures and which is described in the Detailed Description.

The present invention is illustrated in FIG. 2. As shown in FIG. 2, a braided ligature 200 is taken from feed roll 202 by take-off device 205. The feed roll 202 may have a functional brake to facilitate even feeding of the braid to the take-off rolls. Take-off device 205 is not heated and generally will be comprised of one or more rolls, which have multiple wraps of the braided ligature 200 wrapped around the rolls to avoid slippage. The braided ligature 200 is advanced by take-off device 205 which, in a preferred embodiment of this invention, is composed of one or more rolls (i.e., take-off rolls 204 and 206) to a first heating zone, which includes as illustrated, a first set of heated rolls 208 and 210 which are run at substantially the same speed as take-off device (i.e., 204 and 206). Preferably, the braided ligature will be wrapped around heated 208 and 210 to avoid slippage and improve heat transfer. The braided ligature 200 is then advanced to a third heated roll 212 which is rotated a speed faster than the first two heated rolls (208, 210). The second set of heated roll 212 and 213 stretches the ligature 200. The braided ligature is preferably wrapped several times around the third heat roll to avoid slippage and improve heat transfer. The stretched braided ligature 200 is then advanced to the third set of heated rolls. The third set of heated rolls preferably comprises a fifth and sixth heated rolls 214, 216 that are rotated at a speed slower than the second set of heated roll 212 and 213 to control the relaxation of the braided ligature 200. Alternatively the heated rolls 214 and 216 can be rotated at a higher rate of speed to stretch the braided suture a second time. The braided ligatures will preferably be wrapped multiple times around the fifth and sixth heated rolls in a FIG. 8 pattern. The braided ligature 200 is then advanced to tensioning device 218 and proceeds to take up roll 220.

The speed at which the braided ligature travels through the rolls and temperature which the rolls are heated, depends on the size of the braid, braid construction, number of wraps per roll and materials which the braid ligature is made. Generally the overall stretch (i.e., the approximate percent difference in the initial length of the braid as compared to the final length of the braid after the process is finished) will be in the range of from about 3 percent to about 25 percent greater than the initial length of the braid, preferably from about 6 percent to about 20 percent and more preferably from about 10 percent to about 16 percent greater than the initial length of the braid. These percentages are based on the relative speeds between the heated rolls, therefore, are approximate values.

The temperature at which the first three heated rolls are maintained at will be sufficient to facilitate the stretching of the braided ligature. This temperature will generally be in the range of about 150° F. to about 50° F. below the melting temperature of the braided ligature material. As an example, for ligatures made from polyethylene terephthalate, the temperatures will be in the range of from about 150° F. to about 50° F., preferably in the range of from about 125° F. to about 50° F. and most preferably from 100° F. to about 50° F.

After stretching, the braided ligature will then be heat set (and optionally relaxed) by the fifth and sixth heated rolls. The relaxation may be accomplished by matching the speed of the second set of heated rollers (212 and 213), the speeds of the fifth and sixth heated rolls 214 and 216 will be in the range of from about 0 percent to about 15 percent slower than the speed of the second set of heated roller and preferably will be in the range of from about 5 percent to about 15 percent slower than the speed of the second set of heated roller. The percent of relaxation will be approximately the same as the percent reduction in relative speed. Those skilled in the art will appreciate that the individual braided yarns may not be capable of relaxing to the maximum amount specified, in which case the upper limit of the relaxation should be viewed as being the maximum amount that the braid will relax or shrink under the specified conditions or 15 percent whichever is less.

Alternatively, the fifth and sixth heated rolls can perform a heat set and second stretch. The second stretch may be accomplished by increasing the speed of the fifth and sixth heated rollers relative to the speed of the second set of heated roller (212 and 213). For example, for sizes 4/0 through size 2 (USP suture sizes) the hot stretch process could be performed in two or more separate stretching operation as described in the table provided below.

| USP SUTURE SIZE | DOUBLE DRAW CONDITIONS % STRETCH | | | | | |
|---|---|---|---|---|---|---|
| | RANGE | | PREFERRED | | MORE PREFERRED | |
| | DRAW 1 | DRAW 2 | DRAW 1 | DRAW 2 | DRAW 1 | DRAW 2 |
| 4/0 - 2 | about 2 to about 14% | about 2 to about 10% | about 6 to about 12% | about 4 to about 8% | about 8 to about 12% | about 4 to about 8% |

As will be appreciated by those skilled in the art the process of the present invention could be conducted by placing unheated rolls inside an oven or using a heat transfer medium (such as steam) to elevate the temperature of the braided multifilament as it stretched and subsequently heat set using draw rolls.

This process can be used with a variety of biocompatible multifilament braided sutures. Suitable biocompatible multifilament braided sutures may be made from a biocompatible nonabsorbable polymers selected from the group consisting of but not limited to polyethylene, polypropylene homopolymers and copolymers and polymer blends containing polypropylene (such as those described in U.S. Pat. Nos. 3,359,983, 4,520,822, 4,557,264, 4,620,542, 4,621,638 and 4,911,165 hereby incorporated by reference), polyesters such as polyethylene terephthalate, polyamides (i.e. nylon 6, nylon 66, nylon 610 and nylon 4) and combinations thereof. Suitable absorbable materials for the manufacture of multifilament braided sutures may be selected from the group consisting of but are not limited to lactic acid, lactide (including L-, D-, meso and D,L mixtures), glycolic acid, glycolide, caprolactone, p-dioxanone (1,4-dioxan-2-one), trimethylene carbonate (1,3-dioxan-2-one), delta-valerolactone, beta-butyrolactone, epsilon-decalactone, 2,5-diketomorpholine, pivalolactone, alpha, alpha-diethylpropiolactone, ethylene carbonate, ethylene oxalate, 3-methyl-1,4-dioxane-2,5-dione, 3,3-diethyl-1,4-dioxan-2,5-dione, gamma-butyrolactone, 1,4-dioxepan-2-one, 1,5-dioxepan-2-one, 6,6-dimethyl-dioxepan-2-one, 6,8-dioxabicycloctane-7-one and combinations thereof.

Additionally, the braids can be made up of combinations of absorbable and non-absorbable yarns, as well as, from yarns that are combinations of different absorbable and/or different non-absorbable filaments.

Following heat stretching the braided ligatures can be annealed, scoured, coated (i.e. with lubricants, drugs etc.), tipped, attached to needles (or other surgical devices), sterilized and/or packaged using conventional technology.

The following non-limiting examples are illustrative of the principles and practice of this invention. Numerous additional embodiments within the scope and spirit of the invention will become apparent to those skilled in the art.

EXAMPLE 1

Figure 1:
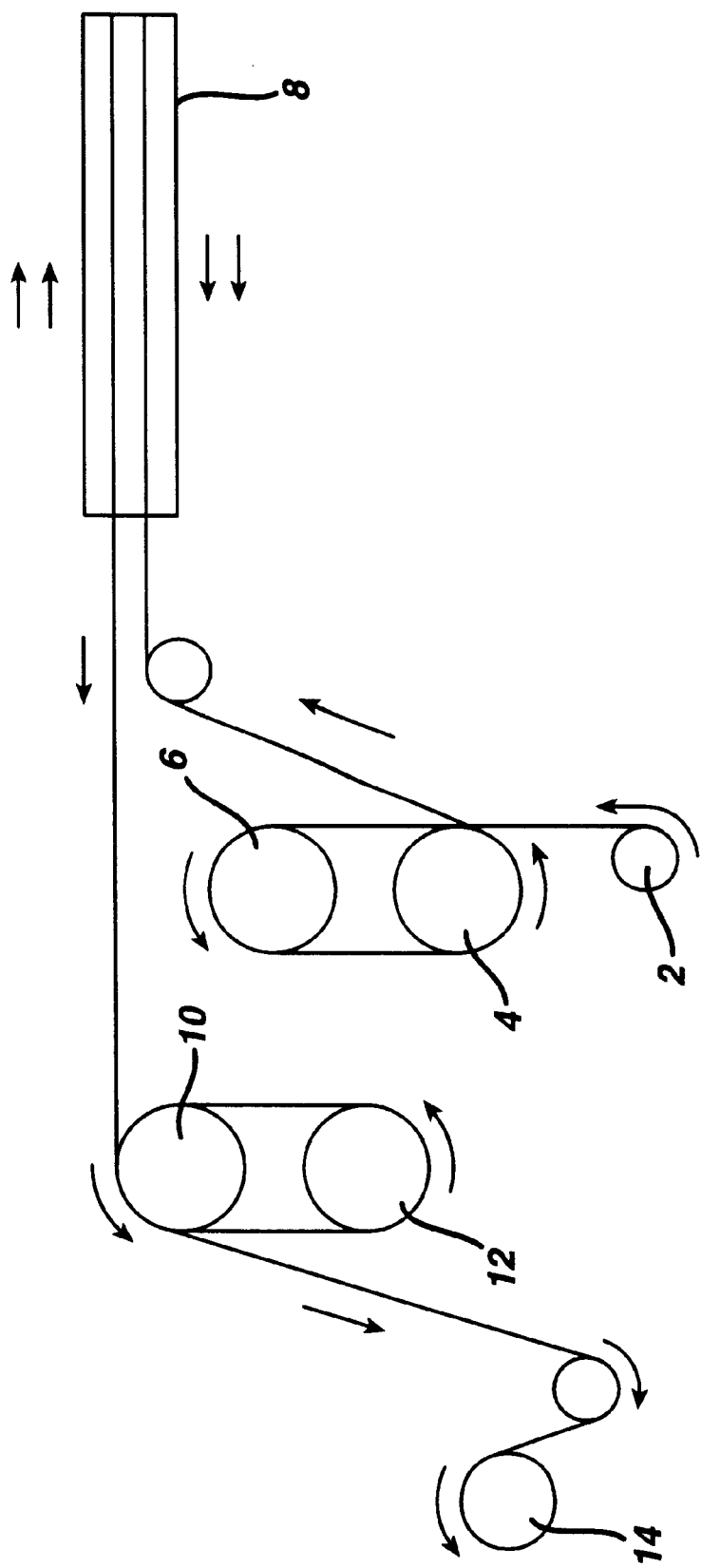
FIG. 1 illustrates a prior art apparatus for hot stretching braided multifilament ligatures.

This example describes a comparative test between the hot stretch machines depicted in FIGS. 1 and 2.

A size 2/0 braided polyester suture was braided using a 16 carrier New England Butt braider. The carrier yarn was nominally 55 denier (2.3 denier per filament polyester fibers) which had been twisted to a nominal level of 8 twists per inch (tpi), and dyed. The yarn used was Trevira™, type 712 from Hoechst Celanese or Hoechst AG. A single core yarn of a nominal 110 denier also twisted to about 8 tpi which was also dyed. The core fiber is threaded in to the braider using a tensioning control device. After the braid was made the braid was taken up on a spool.

The braid was then doffed and wound onto a flexible spring dyer tube for scouring. The braid was scoured in a pressurized vessel with an aqueous detergent under acidic conditions at elevated temperature (165–270° F.) for about three hours. After scouring the braid was dried and a coating was applied to the braid, then the braid was hot stretched.

The braided polyester was hot stretched on the machines described in FIGS. 1 and 2 under the conditions described below in Table 1.

TABLE 1

| | 2-PLATEN AVG./S.D. | HEATED ROLL AVG./S.D. |
|---|---|---|
| IN PROCESS | | |
| TENSILE(lbs) | 13.84/0.389 | 13.86/0.202 |
| ELONGATION % | 13.28/0.747 | 17.105/0.341 |
| KNOT (lbs) | 7.643/0.188 | 7.21/0.188 |
| FINISHED | | |
| TENSILE (lbs) | 14.72/0.27 | 14.59/0.27 |
| ELONGATION % | 12.45/0.99 | 17.4/0.39 |
| KNOT (lbs) | 7.64/0.33 | 7.54/0.43 |
| BUNCH | 5 failures from 200 lots | 0 failures from 60 lots |

As can be seen from the data the number of suture failures per lots because of bunching was reduced.

We claim:

1. A process for hot stretching a braided multifilament comprising
   (a) advancing a braided multifilament to a heated zone, then
   (b) stretching the braided multifilament on rolls while heating the braided multifilament to provide a stretched braided multifilament, thereafter
   (c) heat setting the stretched braided multifilament to provided a braided suture.

2. The process of claim 1 wherein the braided multifilament is stretched in the range of from about 3 percent to about 25 percent of the original length of the braided multifilament.

3. The process of claim 1 wherein the stretched multifilament is relaxed in the range of from about 0 to about 15 percent of the length of the stretched braided multifilament while being heat set.

4. The process of claim 1 wherein the braided multifilament is made of a yarn containing filaments of a biocompatible nonabsorbable polymers selected from the group consisting of polyethylene, polypropylene homopolymers and copolymers and polymer blends containing polypropylene, polyesters, polyamides and combinations thereof.

5. The process of claim 1 wherein the braided multifilament is made of a polyethylene terephthalate yarn.

6. The process of claim 1 wherein the braided multifilament is made of a yarn containing filaments of an absorbable biocompatible polymer or copolymer made from a monomer selected from the group consisting of lactic acid, lactide (including L-, D-, meso and D,L mixtures), glycolic acid, glycolide, -caprolactone, p-dioxanone (1,4-dioxan-2-one), trimethylene carbonate (1,3-dioxan-2-one), delta-valerolactone, beta-butyrolactone, epsilon-decalactone, 2,5-diketomorpholine, pivalolactone, alpha, alpha-diethylpropiolactone, ethylene carbonate, ethylene oxalate, 3-methyl-1,4-dioxane-2,5-dione, 3,3-diethyl-1,4-dioxan-2,5-dione, gamma-butyrolactone, 1,4-dioxepan-2-one, 1,5-dioxepan-2-one, 6,6-dimethyl-dioxepan-2-one, 6,8-dioxabicycloctane-7-one and combinations thereof.

7. The process of claim 1 wherein the braided multifilament is made of a yarn which contains filaments of a copolymer of lactide and glycolide.

8. The process of claim 1 wherein the temperature at which the rolls are maintained at a temperature in the range of from about 15° F. to about 125° F. below the melting point of the polymer in the braided multifilament.

9. The process of claim 1 wherein the braided multifilament is stretched over heated rolls.

10. The process of claim 8 wherein the during the stretched braided multifilament is stretched a second time during heat setting.

11. The process of claim 10 wherein the stretched braided multifilament is stretched in the range of from about 1 to about 10 percent of the length of the stretched braided multifilament.

12. The process of claim 10 wherein the braided multifilament is stretched a first time in the range of from about 2 to about 14 percent and the stretched braided multifilament is stretched a second time and additional 2 to about 10 percent.

13. The process of claim 10 wherein the braided multifilament is stretched a first time in the range of from about 6 to about 12 percent and the stretched braided multifilament is stretched a second time and additional 4 to about 8 percent.

14. The process of claim 10 wherein the braided multifilament is stretched a first time in the range of from about 8 to about 12 percent and the stretched braided multifilament is stretched a second time and additional 4 to about 8 percent.

15. The process of claim 1 wherein the braided suture is sterilized.

16. The process of claim 1 wherein the braided suture is packaged.

17. The process of claim 1 wherein the braided suture is attached to a surgical device.

18. A braided suture made by hot stretching a braided multifilament comprising (a) advancing a braided multifilament to a heated zone, then (b) stretching the braided multifilament on rolls while heating the braided multifilament to provide a stretched braided multifilament, thereafter (c) heat setting the stretched braided multifilament to provided a braided suture wherein the braided multifilament is made of a yarn consisting of filaments of a biocompatible polymer selected from the group consisting of polymers made from monomers selected from the group consisting of polyethylene and polypropylene; homopolymers, copolymers and polymer blends comprising polypropylene, polyesters, polyamides and combinations thereof; and polymers or copolymers made from a monomer selected from the group consisting of lactic acid, lactide (including L-, D-, meso and D,L mixtures), glycolic acid, glycolide, ε-caprolactone, p-dioxanone (1,4-dioxan-2-one), trimethylene carbonate (1,3-dioxan-2-one), delta-valerolactone, beta-butyrolactone, epsilon-decalactone, 2,5-diketomorpholine, pivalolactone, alpha, alpha-diethylpropiolactone, ethylene carbonate, ethylene oxalate, 3-methyl-1,4-dioxane-2,5-dione, 3,3-diethyl-1,4-dioxan-2,5-dione, gamma-butyrolactone, 1,4-dioxepan-2-one, 1,5-dioxepan-2-one, 6,6-dimethyl-dioxepan-2-one and 6,8-dioxabicycloctane-7-one.

19. The braided suture claim 18 wherein the braided multifilament is made of a polyethylene terephthalate yarn.

20. The braided suture of claim 18 wherein the braided multifilament is made of a yarn which contains filament of a copolymer of lactide and glycolide.

21. The braided suture of claim 18 wherein the braided suture is sterilized.

22. The braided suture of claim 18 wherein the braided suture is packaged.

23. The braided suture of claim 18 wherein the braided suture is attached to a surgical device.

* * * * *